United States Patent
Emmett et al.

(10) Patent No.: US 11,839,715 B2
(45) Date of Patent: Dec. 12, 2023

(54) AEROSOL-GENERATING SYSTEM WITH BIOSENSOR

(71) Applicant: PHILIP MORRIS PRODUCTS S.A., Neuchâtel (CH)

(72) Inventors: Robert Emmett, Neuchâtel (CH); Rui Nuno Batista, Morges (CH); Michel bessant, Neuchâtel (CH); Riccardo Riva Reggiori, St Sulpice (CH); Nazan Gunduz, Le Mont sur Lausanne (CH)

(73) Assignee: Philip Morris Products S.A., Neuchâtel (CH)

( * ) Notice: Subject to any disclaimer, the term of this patent is extended or adjusted under 35 U.S.C. 154(b) by 717 days.

(21) Appl. No.: 16/979,718

(22) PCT Filed: Mar. 13, 2019

(86) PCT No.: PCT/IB2019/052053
§ 371 (c)(1),
(2) Date: Sep. 10, 2020

(87) PCT Pub. No.: WO2019/175810
PCT Pub. Date: Sep. 19, 2019

(65) Prior Publication Data
US 2021/0037889 A1 Feb. 11, 2021

(30) Foreign Application Priority Data
Mar. 14, 2018 (EP) .................................... 18161858

(51) Int. Cl.
*A24F 40/00* (2020.01)
*A61M 15/06* (2006.01)
(Continued)

(52) U.S. Cl.
CPC .............. *A61M 15/06* (2013.01); *A24F 40/00* (2020.01); *A24F 40/51* (2020.01); *A24F 40/60* (2020.01);
(Continued)

(58) Field of Classification Search
CPC .......... A24F 40/65; A24F 40/95; A24F 40/51; A24F 40/60; A24B 5/0022; A24B 5/0265
See application file for complete search history.

(56) References Cited

U.S. PATENT DOCUMENTS 7,458,374 B2   12/2008   Hale et al.
8,495,998 B2    7/2013   Schennum
(Continued)

FOREIGN PATENT DOCUMENTS

CA   2998563 A1   4/2017
EP   2444112      4/2012
(Continued)

OTHER PUBLICATIONS

Chinese Office Action for CN Application No. 201980014626.9, issued by the China National Intellectual Property Administration dated Feb. 28, 2022; 16 pgs. including English translation.
(Continued)

*Primary Examiner* — Phuong Chi Thi Nguyen
(74) *Attorney, Agent, or Firm* — Mueting Raasch Group

(57) ABSTRACT

An aerosol-generating system has a biosensor configured to detect a biological characteristic of the user. A controller provides health data based on the at least one biological characteristic detected by the biosensor. The health data may be provided to the user, used to modify an aerosol delivery profile of an aerosolizer, stored for later use, or may be communicated to other devices.

20 Claims, 4 Drawing Sheets

(51) Int. Cl.

| | |
|---|---|
| *A24F 40/65* | (2020.01) |
| *A24F 40/95* | (2020.01) |
| *A24F 40/51* | (2020.01) |
| *A24F 40/60* | (2020.01) |
| *A61B 5/00* | (2006.01) |
| *A61B 5/0205* | (2006.01) |
| *A61B 5/11* | (2006.01) |
| *A61B 5/1455* | (2006.01) |
| *A61B 5/021* | (2006.01) |
| *A61B 5/024* | (2006.01) |
| *A61B 5/053* | (2021.01) |
| *G06F 3/14* | (2006.01) |
| *A24F 40/20* | (2020.01) |

(52) U.S. Cl.
CPC .............. *A24F 40/65* (2020.01); *A24F 40/95* (2020.01); *A61B 5/0022* (2013.01); *A61B 5/0205* (2013.01); *A61B 5/11* (2013.01); *A61B 5/14551* (2013.01); *A61B 5/6887* (2013.01); *A61B 5/742* (2013.01); *A24F 40/20* (2020.01); *A61B 5/021* (2013.01); *A61B 5/02416* (2013.01); *A61B 5/053* (2013.01); *G06F 3/14* (2013.01)

(56) References Cited

U.S. PATENT DOCUMENTS

| | | |
|---|---|---|
| 2003/0209240 A1 | 11/2003 | Hiale et al. |
| 2005/0251289 A1 | 11/2005 | Bonney et al. |
| 2007/0038330 A1 | 2/2007 | Sullivan |
| 2007/0085341 A1* | 4/2007 | Walmsley ............... F16L 21/08 285/369 |
| 2010/0288589 A1* | 11/2010 | Emmett ............... F16D 65/092 188/73.1 |
| 2010/0319686 A1 | 12/2010 | Schennum |
| 2012/0281392 A1* | 11/2012 | Workman ............... H02J 7/35 362/183 |
| 2014/0107493 A1 | 4/2014 | Yuen et al. |
| 2016/0158471 A1 | 6/2016 | Fink et al. |
| 2016/0211693 A1 | 6/2016 | Stevens et al. |
| 2017/0049154 A1* | 2/2017 | Batista ............... H05B 1/0244 |
| 2018/0021328 A1 | 1/2018 | Myers et al. |
| 2021/0037889 A1* | 2/2021 | Emmett ............... A61B 5/6887 |
| 2022/0144752 A1* | 5/2022 | Seo ............... G08B 21/18 |
| 2022/0248761 A1* | 8/2022 | Emmett ............... A24F 40/48 |
| 2023/0225411 A1* | 7/2023 | Batista ............... H05B 6/108 131/328 |

FOREIGN PATENT DOCUMENTS

| | | |
|---|---|---|
| RU | 2691615 C2 | 6/2019 |
| WO | 20160001926 | 1/2016 |
| WO | WO 2017/055795 A1 | 4/2017 |
| WO | WO 2018/075981 A2 | 4/2018 |

OTHER PUBLICATIONS

Japanese Decision to Grant for JP Application No. 2020-544637 issued by the Japanese Patent Office dated Feb. 15, 2023; 2 pgs. No English translation available.

Russian Office Action for RU Application No. 2020130049 issued by the Patent Office of the Russian Federation dated May 18, 2022; 19 pgs. including English translation.

European Extended Search Report for EP 18161858.8, issued by the European Patent Office dated Aug. 22, 2018; 6 pgs.

International Search Report and Written Opinion for PCT/IB2019/052053; issued by the European Patent Office dated Jun. 14, 2019; 8 pgs.

International Preliminary Report on Patentability for PCT/IB2019/052053; issued by the European Patent Office dated Feb. 7, 2020; 16 pgs.

"Elfi-Tech Sensor Technology" [online]; Mar. 8, 2018; http://elfi-tech.com/tech/; 2 pgs.

"Leman Micro Devices" [online]; Mar. 8, 2018; http://leman-micro.com; 2 pgs.

* cited by examiner

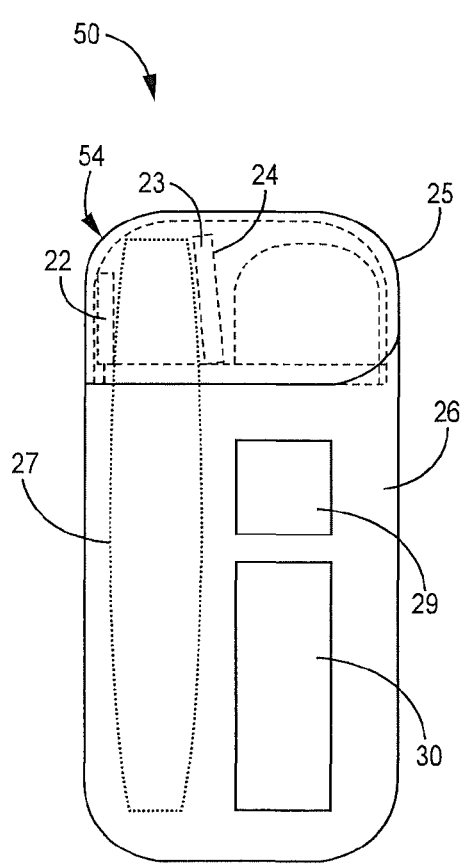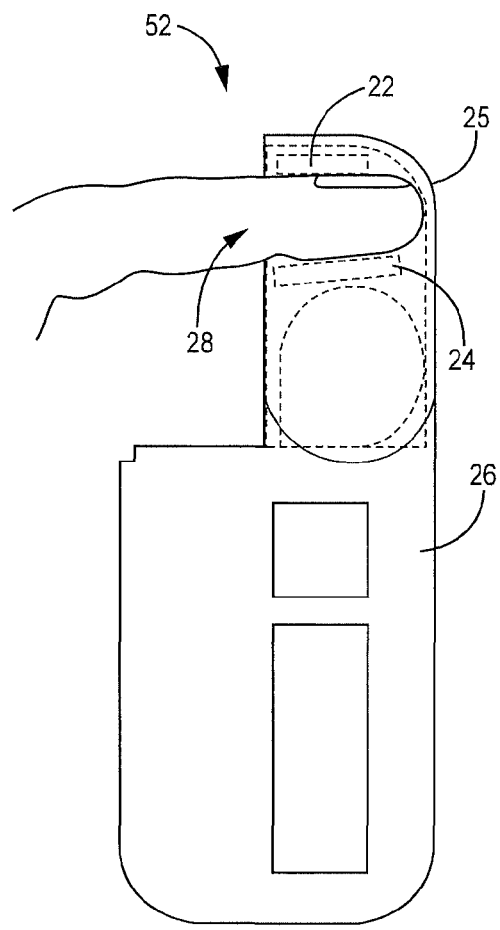
FIG. 2A  FIG. 2B

AEROSOL-GENERATING SYSTEM WITH BIOSENSOR

This application is the § 371 U.S. National Stage of International Application No. PCT/IB2019/052053, filed 13 Mar. 2019, which claims the benefit of European Application No. 18161858.8, filed 14 Mar. 2018, the disclosures of which are incorporated by reference herein in their entireties.

The present disclosure relates to aerosol-generating systems and, more particularly, to aerosol-generating systems having at least one biosensor that may be used to modify aerosol delivery.

There is increasing demand for handheld aerosol-generating systems or devices that are able to deliver aerosol for user inhalation. Some aerosol-generating devices operate by heating an aerosol-forming substrate with a heating element. In particular, some devices operate by inserting an electrical heater into a solid aerosol-forming substrate and supplying power to the heater from a battery included in the device. Aerosol-generating devices may produce aerosol from an aerosol-forming substrate in response to a user action, such as a puff. Users typically hold aerosol-generating devices while puffing and in between puffs.

There is also increasing demand for wearable to provide users with more information about their health. Health information may be of special interest to users in certain situations.

It would be desirable to provide an aerosol-generating system that can provide aerosol and health information for the user. It would be desirable to allow for the adjustment of the delivery of aerosol to the user based on health information. It would be desirable to allow health information to be used as health data in various ways to benefit the user.

Various aspects of this disclosure relate to an aerosol-generating system having a biosensor configured to detect a biological characteristic of the user. A controller provides health data based on the at least one biological characteristic detected by the biosensor when the controller is operatively connected to the biosensor. The health data may be provided to the user, used to modify an aerosol delivery profile of an aerosolizer, stored for later use, or may be communicated to other devices. Health data may be used in various situations, for example, related to: transitioning from conventional smoking articles, exercising or competing, medical interventions or treatments, experiencing stressful conditions, taking medical prescriptions, or having other physical conditions (for example, pregnancy).

In one aspect of the disclosure, an aerosol-generating system includes a housing configured to be held by a user. The system also includes an aerosolizer coupled to the housing and configured to produce aerosol from an aerosol-forming substrate having nicotine. The system also includes a charging unit operatively couplable to the housing. The system also includes a biosensor integrated into the charging unit and configured to detect at least one biological characteristic of the user. The system also includes a controller configured to activate the aerosolizer. The controller is also configured to provide health data based on the at least one biological characteristic detected by the biosensor.

In one or more aspects, the controller is configured to modify an aerosol delivery profile based on the health data.

In one or more aspects, the controller is configured to automatically modify the aerosol delivery profile based on the health data.

In one or more aspects, to modify the aerosol delivery profile includes the controller using one of a plurality of pre-programmed aerosol delivery profiles stored on the controller.

In one or more aspects, the system includes a display operatively couplable to the controller configured to display graphics based on the health data.

In one or more aspects, the controller includes a communication interface configured to operatively communicate the health data to at least one of the charging unit of the aerosol-generating system and a separate user interface.

In one or more aspects, the communication interface is configured to communicate health data to an Internet-enabled device.

In one or more aspects, the biosensor is accessible by the user when using the aerosolizer.

In one or more aspects, the biosensor includes at least one of a contact blood pressure sensor, a photoplethysmography electronic, an oximeter electronic set, a non-invasive laser sensor, a bio-impedance monitor, and a motion detector.

In one or more aspects, the photoplethysmography electronic set is positioned on the charging unit.

In one or more aspects, the oximeter electronic set is positioned on the charging unit.

In one or more aspects, the oximeter electronic set is contained in a reclosable housing of the charging unit.

In one or more aspects, the oximeter electronic set defines a recess in the reclosable housing configured to receive a finger of the user to detect the at least one biological characteristic of the user.

In one or more aspects, the at least one biological characteristic includes at least one of a blood pressure, a heart rate, an oxygen saturation, a carbon monoxide saturation, and a movement indicator.

In one or more aspects, the controller includes a memory configured to store the health data.

Advantageously, the aerosol-generating system of the present disclosure allows the user to monitor health data conveniently, even while using an aerosol-generating device of the system. The available health data may help the user make informed choices about use of the aerosol-generating system. For example, the health data may be used to determine or select an appropriate aerosol-delivery profile. The aerosol-generating system may even automatically select the appropriate aerosol-delivery profile for the user to further add to convenience. Providing health data may even help the user to become of health statuses that were previously unknown to the user. Other advantages and benefits will become apparent to one skilled in the art having the benefit of this disclosure.

All scientific and technical terms used herein have meanings commonly used in the art unless otherwise specified. The definitions provided herein are to facilitate understanding of certain terms used frequently herein.

The term "aerosol-generating device" refers to a device configured to use an aerosol-forming substrate to generate aerosol. In some embodiments, the aerosol-generating device may be described as a smoking article or a holder, particularly a tobacco stick holder. Preferably, the aerosol-generating device also includes an aerosolizer. The aerosolizer may include an atomizer, cartomizer, heater, or other aerosolizing components.

The term "aerosol-forming substrate" refers to a device or substrate that releases compounds that may form an aerosol to be inhaled by a user. In some cases, the substrate may release volatile compounds upon heating. Preferably, the aerosol-forming substrate includes nicotine. Suitable aerosol-forming substrates may include plant-based material. For example, the aerosol-forming substrate may include tobacco or a tobacco-containing material containing volatile tobacco flavor compounds, which are released from the aerosol-forming substrate upon heating. In addition, or alternatively, an aerosol-forming substrate may include a non-tobacco containing material. The aerosol-forming substrate may include homogenized plant-based material. The aerosol-forming substrate may include at least one aerosol former. The aerosol-forming substrate may include other additives and ingredients such as flavorants. In some embodiments, the aerosol-forming substrate is a liquid at room temperature. For example, the aerosol forming substrate may be a liquid solution, suspension, dispersion or the like. A liquid aerosol-forming substrate may include glycerol, propylene glycol, water, nicotine and, optionally, one or more flavorants. In some embodiments, the aerosol-forming substrate is a solid at room temperature, such as a tobacco stick or nicotine powder.

The term "tobacco material" refers to a material or substance including tobacco, which includes tobacco blends or flavored tobacco, for example.

Having defined certain frequently-used terms above, aerosol-generating systems of the present disclosure will be described herein in more detail. In general, the aerosol-generating systems each include a biosensor configured to detect a biological characteristic. Health data based on the biological characteristic may be determined. The health data may be used to modify an aerosol delivery profile or may be used in other ways that interest the user.

The aerosol-generating system may include one or more housings configured to be held by a user. In some embodiments, the system may include an aerosol-generating device having a housing. In some embodiments, the system may also include a charging unit having a separate housing. The housing of the aerosol-generating device may be configured to couple to the housing of the charging unit, for example, to be received by the charging unit.

The aerosol-generating device may include a battery. When operatively coupled together, the charging unit may recharge the aerosol-generating device. The charging unit may include a battery having a greater capacity than the battery of the aerosol-generating device.

The aerosol-generating device includes an aerosolizer. The aerosolizer is contained by the housing when used. The aerosolizer is configured to produce aerosol from an aerosol-forming substrate.

Any suitable type of aerosolizer may be used. In some cases, the aerosolizer may be thermally or fluidly coupled to the aerosol-forming substrate. The aerosolizer may be compatible for use with various types of aerosol-forming substrates.

The aerosolizer may include a heating blade for use with a solid aerosol-forming substrate. The heating blade may be coupled to the housing of the aerosol-generating device to receive electrical power from a power source (battery). For example, the aerosol-forming substrate may be provided in the form of a heat stick. The heating blade may be inserted into the heat stick and heated to produce aerosol from the solid substrate. The solid substrate may be a smoking material, such as tobacco. The heat provided by the heating blade to the heat stick may not burn the smoking material.

The aerosolizer may include a heater, a heater coil, a chemical heat source (such as a carbon heat source), or any suitable means that heats the substrate to generate aerosol. The aerosolizer may be coupled to the housing of the aerosol-generating device to receive electrical power from a power source (battery) and may be disposed adjacent to the substrate. For example, a heating element of a heater may be disposed adjacent to the aerosol-forming substrate and heated to produce aerosol from a liquid or solid substrate. A heater coil may include a susceptor adjacent to the aerosol-forming substrate and when an energized inductive coil is disposed adjacent to the susceptor, electromagnetic energy may be transferred to the susceptor to heat the substrate.

The aerosolizer may include an atomizer. A liquid aerosol-forming substrate may be contained in the substrate housing and in fluid communication with the atomizer. The atomizer may mechanically generate aerosol from the liquid substrate instead of relying only on temperature.

The aerosolizer may be compatible for use with an aerosol-forming substrate having a nicotine source and a lactic acid source. The nicotine source may include a sorption element, such as a PTFE wick with nicotine adsorbed thereon, which may be inserted into a chamber forming a first compartment. The lactic acid source may include a sorption element, such as a PTFE wick, with lactic acid adsorbed thereon, which may be inserted into a chamber forming a second compartment. The aerosolizer may include a heater to heat both the nicotine source and the lactic acid source. Then, the nicotine vapor may react with the lactic acid vapor in the gas phase to form an aerosol.

The aerosolizer may be compatible for use with an aerosol-forming substrate having a capsule that contains nicotine particles and disposed in a cavity. During a user's inhalation, the air flow may rotate the capsule. The rotation may suspend and aerosolize the nicotine particles.

The aerosol-forming substrate is at least partially disposed in the aerosol-generating device when used. The aerosol-forming substrate may be removable after being consumed. A new aerosol-forming substrate may be received by the aerosol-generating device to replace the consumed substrate.

The aerosol-generating system includes one or more biosensors configured to detect at least one biological characteristics of the user. The biosensor may include any suitable sensor capable of detecting biological characteristics of interest to the user. For example, the biological characteristic may include at least one of a blood pressure, a heart rate, an oxygen saturation, a carbon monoxide saturation, and a movement indicator (such as a step count). The biosensor may include at least one of a contact blood pressure sensor, a photoplethysmography electronic, an oximeter electronic set, a non-invasive laser sensor, a bio-impedance monitor, and a motion detector (such as an accelerometer or other mechanism to measure a step count or other movement).

Various correlations between biological characteristics may be determined by monitoring more than one biological characteristic. In some embodiments, biological characteristics may be monitored or detected to correlate vital signs and stress indicators. For example, one or more biosensors may monitor or detect at least heart rate, movement, and blood pressure, which may be used to correlate the vital signs to a stress status.

In general, the aerosol-generating system may use the biosensors to collect health data in real time. Preferably, the aerosol-generating system need not rely on separate devices to collect health data. In one example, the aerosol-generating device itself is capable of collecting health data, for example, without using the charging unit, or vice versa.

Biological characteristics may be used to determine health data. Health data may help the user monitor for health conditions, which may be known or unknown by the user. Based on the health data, a particular aerosol delivery profile may be desirable. The aerosol delivery profile may be selected by the user or automatically by the aerosol-generating system.

An oximeter electronic set can read the users peripheral blood oxygen saturation ($SpO_2$) or carbon monoxide (CO) saturation from arterial blood gas analysis. In some embodiments, a first part of the oximeter electronic set (a light source) may be placed on a thin part of the user's body, such as the finger. For example, suitable light sources include one or more light-emitting diodes (LEDs). At least two wavelengths of light may be passed through the body part to a second part of the electronic set (a photodetector or photodiode). The changing absorbance at each of the wavelengths may be used to determine absorbances due to arterial blood apart from other tissues. The oximeter electronic set may be used to measure heartrate, oxygen saturation, carbon monoxide saturation (for example, using CO-oximetry), or both.

An oximeter electronic set may be considered a specific type of photoplethysmography (PPG) electronic set, or vice versa. In general, a photoplethysmography (PPG) electronic set can detect blood volume changes in the microvascular bed of tissue, which may be used to determine heart rate or oxygen saturation, using light.

Some oximeter or PPG electronic sets may be described as transmissive electronic sets, in which the light source and the photodetector are on opposing sides of the user's body part. Other oximeter or PPG electronic sets may be described as reflective electronic sets, in which the light source and the photodetector are on the same or adjacent side of the user's body part.

A contact blood pressure sensor may be used to monitor a blood pressure. The contact blood pressure sensor may include at least a light source and a light detector. One example of a contact blood pressure sensor is the LMD health sensor commercially available from Leman Micro Devices, Lausanne, Switzerland.

A bio-impedance monitor may be used to detect heartrate. The bio-impedance monitor may include, for example, at least two conductive contact pads for electrical coupling to the user's skin.

A non-invasive laser sensor may use laser-scattering to detect blood flow, hemodynamic indices, blood pressure, heart rate, heart rate variability, or respiration. One example of a non-invasive laser sensor is the sensor commercially available from Elfi-Tech, Science Park, Rehovot, Israel.

The accelerometer is an instrument for measuring acceleration. An example of an accelerometer is a 3-axis accelerometer set that measures acceleration in three directions. The accelerometer may be used to determine at least a step count. The accelerometer may also be used for collecting other movement-related information of interest to the user.

The biosensor is accessed by the user when in use. Preferably, the biosensor is accessible by the user when using the aerosolizer. At least one biosensor may be coupled to, positioned on, or integrated into the housing of the aerosol-generating device. In one example, the biosensor includes a photoplethysmography electronic set that is positioned on the housing containing the aerosolizer. The biosensor on the housing of the aerosol-generating device may form part of an outer surface of the housing. While the user is holding the device to use the aerosolizer, the user may engage the biosensor of the aerosol-generating device by hand. The photoplethysmography electronic set may be a reflective photoplethysmography electronic set. The light source and the photodetector of the reflective photoplethysmography electronic set are configured to be on the same side of the user's finger.

The controller may sample, or measure, the biological characteristics on a regular basis or under certain conditions. In some embodiments, the user may provide an input detected by the controller that causes the controller to make a measurement at a certain point in time or during a defined period of time, for example.

Additionally, or alternatively, at least one biosensor may be coupled to, positioned on, or integrated into the charging unit. The charging unit may be larger than the aerosol-generating device and may accommodate sensors having a particular geometry or size in one or more dimensions in an ergonomic manner that would be difficult to accommodate in the aerosol-generating device. A housing of the charging unit may be configured, or structured, such that a human finger may be inserted into the housing for measurement by the biosensor. In one or more embodiments described herein, the biosensor includes an oximeter electronic set contained in a reclosable housing of the charging unit. In particular, the housing of the charging unit may include a body portion and a lid portion. In one example, the biosensor may be positioned on the interior of the lid portion. The lid portion may be opened to provide access to the biosensor. The biosensor may define a recess in the reclosable housing configured to receive a finger of the user to detect the at least one biological characteristic of the user. While the user is using the aerosolizer, the user may be free to insert one finger into the recess of the biosensor to engage the biosensor of the charging unit by hand. The light source and the photodetector of the oximeter electronic set (or transmissive photoplethysmography electronic set) are configured to be on opposite sides of the user's finger.

The aerosol-generating device may include a controller. The controller may be operatively coupled to the aerosolizer. When the aerosol-generating device includes a biosensor, the controller may also be operatively coupled to the biosensor. The controller of the aerosol-generating device may be contained by the housing of the aerosol-generating device. The controller is configured to activate the aerosolizer to produce aerosol from the aerosol-forming substrate. The aerosolizer may be activated to produce aerosol according to an aerosol delivery profile.

The charging unit may include a controller separate from the controller of the aerosol-generating device. When the charging unit includes a biosensor, the controller may also be operatively coupled to the biosensor. The controller of the charging unit may be contained by the housing of the charging unit.

The functionality described herein with respect to the biosensors and health data may be carried out by one or more controllers, for example, in the aerosol-generating device or the charging unit. In particular, one or more of the controllers are configured to provide health data based on the at least one biological characteristic detected by the biosensor when operatively connected to the biosensor.

The health data determined from the detected biological characteristics may be communicated between the aerosol-generating device and the charging unit. In one example, one or more of the controllers includes a communication interface configured to operatively communicate the health data. The communication interface of the aerosol-generating device, for example, may be configured to communicate health data to at least one of the charging unit and a separate user interface. The separate user interface may be part of a device separate from the aerosol-generating system, such as a smartphone, tablet, or wearable device of the user (for example, a smartwatch). The separate user interface may include a display or a speaker to relay information to the user, for example using graphics or audio. The health data may also be used as an input to one or more applications running on the separate user interface.

The separate user interface may be an Internet-enabled device. Health data may be communicated to the Internet-enabled device, which may communicate the health data over the Internet for remote storage or use. For example, health data may be stored on a remote server. The remote server may be used to further process the data or store it for later access, for example, by the user on a cloud-based data interface.

The communication interface may be any suitable interface, wired or wireless, configured to communicate data between devices, such as universal serial bus (USB), powerline, Wi-Fi, Bluetooth, and cellular data networks.

Various devices may be connected to the communication interface or removed over time. The communication interface may be configured to receive data from other devices. Such received data may be provided to the user, for example, using a user interface of the aerosol-generating system.

The aerosol-generating system may also include one or more user interfaces to provide health data to the user. In some embodiments, a display or a speaker is operatively coupled to one or more of the controllers. The display may be configured, for example, to display graphics based on the health data. Graphics may include alphanumerical characters or other images.

One or more controllers may include memory. The memory may be used to store various types of data, such as the health data. Stored health data may be later used, displayed, or communicated. In one example, health data may be determined and stored on the controller of the aerosol-generating device. In another example, health data may be determined and stored on the controller of the charging unit. In further examples, health data may be communicated from the aerosol-generating device to the charging unit and stored, or vice versa.

Health data may be used by the controller to modify the aerosol delivery profile. The aerosol delivery profile describes how the aerosol is generated from the aerosol-forming substrate and delivered to the user. For example, the aerosol delivery profile may adjust the activation of the aerosolizer to increase or reduce the amount of aerosol being generated. In some embodiments, the aerosol delivery profile includes a nicotine delivery profile. The nicotine delivery profile may describe how much nicotine is being delivered to the user.

Depending on the user's health data or preferences, the amount of aerosol or nicotine desired may increase or decrease. Health data may be used as an input into selecting the appropriate aerosol or nicotine delivery profile that is desired by the user.

The aerosol delivery profile may be selected from a plurality of pre-programmed aerosol delivery profiles. The pre-programmed aerosol delivery profiles may be stored on the memory of the controller or communicated to the controller, for example, from another controller or user device (for example, a smartphone). Each aerosol delivery profile may be appropriate for different health statuses of the user that can be determined from the health data.

The user may be presented with health data and make an aerosol delivery profile selection. Additionally, or alternatively, one of the controllers may automatically modify the aerosol delivery profile based on the health data. For example, the controller may select the appropriate aerosol delivery profile when certain based on particular values or thresholds related to the health data.

Some users may be interested in monitoring their health data, for example, to build historical records of their experiences with the aerosol-generating device. Having such health and historical data may be useful for users attempting to transition from conventional smoking articles to handheld aerosol-generating devices.

Some users may participate in events that elevate the heartrate. For example, some users may engage in regular physical exercise or sporting competitions, such as marathons and triathlons. As another example, some users may undergo medical interventions or treatments, which may be surgical or otherwise invasive. Such users may be interested in monitoring their health data before or after such events. In particular, users may wish to wait for a target heartrate after such events before beginning to use the aerosol-generating system.

Some users may have a health status or may take medication that may be influenced by nicotine intake. For example, some users may be recovering from high or post-traumatic stress. Such users may wish to monitor their health data to coordinate their use of the aerosol-generating device.

Some users may be uncertain of their health status. Monitoring health data, including while using the aerosol-generating device, may help the user to become aware of their own health status.

In general, the aerosol delivery profile may be adapted based on health data indicating various health statuses of the user. The user may allow the controller to automatically modify the aerosol delivery profile or may select the desired aerosol delivery profile. In one example, the user may select a desired amount, or threshold, of nicotine, which may be used by the controller to select an appropriate aerosol delivery profile that meets the desired amount or threshold. With pre-programmed aerosol delivery profiles being stored on the controller, the user may be prompted to select from the available profiles or the controller may automatically select one.

The controller may be provided in any suitable form and may, for example, include a processor and a memory. Generally, the controller includes memory that contains instructions that cause one or more components to carry out a function or aspect of the controller. Functions attributable to controller in this disclosure may be embodied as one or more of software, firmware, and hardware.

In particular, one or more of the components, such as controllers, described herein may include a processor, such as a central processing unit (CPU), computer, logic array, or other device capable of directing data coming into or out of the controller. The controller may include one or more computing devices having memory, processing, and communication hardware. The controller may include circuitry used to couple various components of the controller together or with other components operably coupled to the controller. The functions of the controller may be performed by hardware and/or as computer instructions on a non-transient computer readable storage medium.

The processor of the controller may include any one or more of a microprocessor, a microcontroller, a digital signal processor (DSP), an application specific integrated circuit (ASIC), a field-programmable gate array (FPGA), and/or equivalent discrete or integrated logic circuitry. In some examples, the processor may include multiple components, such as any combination of one or more microprocessors, one or more controllers, one or more DSPs, one or more ASICs, and/or one or more FPGAs, as well as other discrete or integrated logic circuitry. The functions attributed to the controller or processor herein may be embodied as software, firmware, hardware, or any combination thereof. While described herein as a processor-based system, an alternative controller could utilize other components such as relays and timers to achieve the desired results, either alone or in combination with a microprocessor-based system.

In one or more embodiments, the exemplary systems, methods, and interfaces may be implemented using one or more computer programs using a computing apparatus, which may include one or more processors and/or memory. Program code and/or logic described herein may be applied to input data/information to perform functionality described herein and generate desired output data/information. The output data/information may be applied as an input to one or more other devices and/or methods as described herein or as would be applied in a known fashion. In view of the above, it will be readily apparent that the controller functionality as described herein may be implemented in any manner known to one skilled in the art.

The controller may be configured to regulate a supply of power. For example, the power supplied to the aerosolizer may be managed by the controller, for example, to regulate the generation of aerosol from the aerosol-forming substrate.

In one or more embodiments described herein, an aerosol-generating system includes a housing configured to be held by a user. The system also includes an aerosolizer configured to produce aerosol from an aerosol-forming substrate. The system also includes a biosensor configured to detect at least one biological characteristic of the user. The system also includes a controller configured to activate the aerosolizer. The controller is also configured to provide health data based on the at least one biological characteristic detected by the biosensor.

FIGS. 1A-B are illustrations showing an example of one aerosol-generating device of the aerosol-generating system in a cross-section view and a bottom view, respectively.

FIGS. 2A-B are illustrations showing an example of one charging unit of the aerosol-generating system in a closed position and an open position, respectively.

Figure 1A:
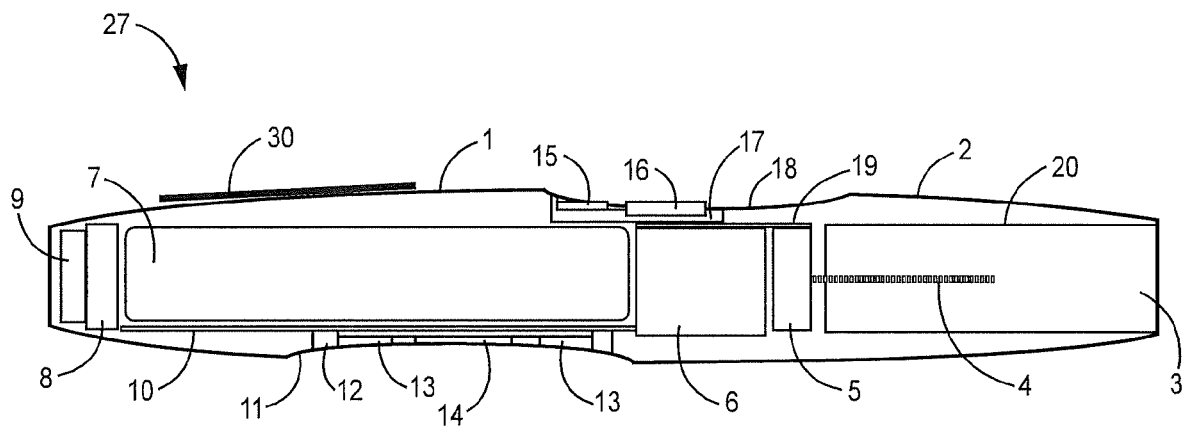
Figure 1B:
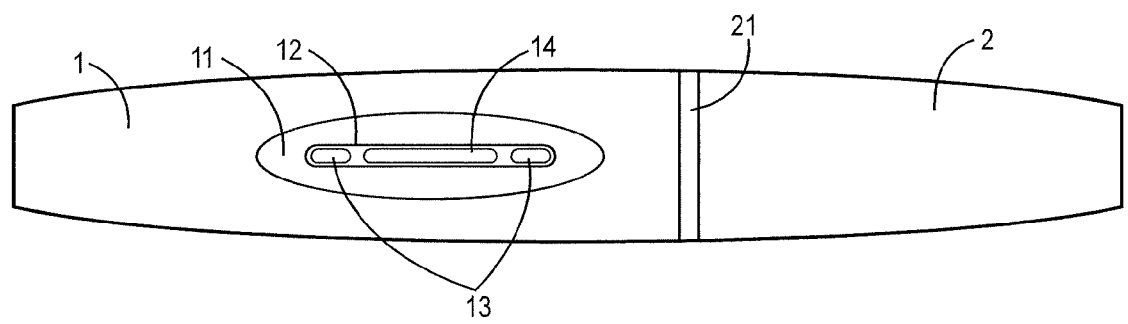

FIGS. 1A-B show aerosol-generating device 27 including main tobacco stick holder 1, or controller portion, and cover 2, or mouth portion. Main tobacco stick holder 1 and cover 2 together define the housing of aerosol-generating device 27. Cover 2 defines cavity 3, which is configured to receive a tobacco heat stick (not shown). The tobacco heat stick may be pierced by heating element 4 (aerosolizer) when inserted into cavity 3. Heating element 4 is provided in the form of a blade or pin, for example, and utilizes a resistor for resistive heating or a susceptor for induction heating. Heating element 4 raises the temperature of the tobacco heat stick when activated. Holder 5, or base of heating element 4, provides electrical connectivity (operative coupling) between heating element 4 and electronic control unit 6 (controller). Electronic control unit 6 is operatively coupled to power supply 7, which includes a battery or batteries. Electronic control unit 6 is used to activate, or to deliver power to, the heating element. Electrical unit 8 (communication interface) with a printed circuit board is operatively coupled to electronic control unit 6 and power supply 7. Electrical unit 8 is operatively coupled to electrical or data contact pads 9, which may be used to couple to an external power supply for charging and an external device for communicating data. Connectivity substrate 10, or the wiring of a flat flexible substrate, may be used to operatively couple electrical unit 8 and electronic control unit 6.

Recessed surface 11 is provided on main tobacco stick holder 1 to provide ergonomic contact with biosensor 12 and light-emitting diodes 13 for the user's fingers. Recessed surface 11 may also provide some protection for biosensor 12 (for example, a reflective electronic set). Biosensor 12 includes light-emitting diodes 13 (light source) provided in the recessed surface 11. Light-emitting diodes 13 may be green LEDs, which may also emit in the infrared (IR) spectrum. Biosensor 12 also includes one or more sensors 14, which read IR and/or green light that is emitted and reflected, which may be used for photoplethysmography or other biosensing.

Light-emitting diode 15 is provided along main tobacco stick holder 1 and provides status indications, such as on/off or an operating mode. Light-emitting diode 15 may be color coded to provide such indications. Operating button 16, or actuator, is provided along main tobacco stick holder 1 and allows the user to turn aerosol-generating device 1 on or off, as well as access certain menu modes. Light-emitting diode 15 and operating button 16 are operatively coupled to printed circuit board 17. Printed circuit board 17 is operatively coupled to electronic control unit 6 through connectivity substrate 19, or the wiring of a flat flexible substrate. Recessed surface 18 is provided along main tobacco stick holder 1 to provide ergonomic contact with, and protection of, light-emitting diode 15 and operating button 16 for the user's fingers. In particular, recessed surface 18 provides some protection from unintended actuation of operating button 16. Main tobacco stick holder 1 includes display 30 (user interface), which may display alphanumeric graphics or other graphics visible to the user.

Cavity housing 20 defines cavity 3 and provides air management around the tobacco heat stick when inserted into cavity 3. Cavity housing 20 may also be used to extract the tobacco heat stick from the aerosol-generating device 1. As can be seen in FIG. 1B, aerosol-generating device 27 can be formed of two parts, main tobacco stick holder 1 and cover 2 joined together by joint 21. Joint 21 may provide a water-proof or water-resistant coupling between holder 1 and cover 2 to provide a water-proof or water-resistant housing, respectively.

FIGS. 2A-B show aerosol-generating system 50 including charging unit 52, which includes cover 25 (lid) and main charging unit 26 (body). Cover 25 may be opened (FIG. 2A) or closed (FIG. 2B). Cover 25 opens smoothly at least up to 90 degrees to provide sufficient clearance for the user's finger. When cover 25 is opened, the user may access biosensor 54. In particular, the user may insert a finger into recess 28 formed by biosensor 54. Cover 25 defines a cavity with sufficient inner volume to accommodate biosensor 54 and other electronic components, as well as recess 28 for receiving the user's finger (an adult finger). As illustrated, biosensor 54 is an oximeter electronic set. Biosensor 54 includes light-emitting diode 22 and sensor 23. Light-emitting diode 22 serves as the light source for oximetry. Sensor 23 includes one or more light-sensitive photodiodes to read light through the finger of the user for oximetry. Sensor 23 is disposed on spring 24, which may help to comfortably accommodate the user's finger. Spring 24 may be a hard metal alloy formed into a flat blade.

As shown in FIG. 2A, aerosol-generating device 27 may be inserted into charging unit 52. Cover 25 may be closed to contain and protect aerosol-generating device 27 when charging. Part of aerosol-generating device 27 is contained in recess 28. Main charging unit 26 includes electronic control unit 29 (controller) and power supply 30, which includes a battery or batteries. Power supply 30 is typically larger and contains more charge than power supply 7 (FIGS. 1A-B). Although not shown, charging unit 52 may include a communication interface, wired or wireless, that communicates with aerosol-generating device 27, for example using electrical unit 8 (FIGS. 1A-B).

Figure 3:
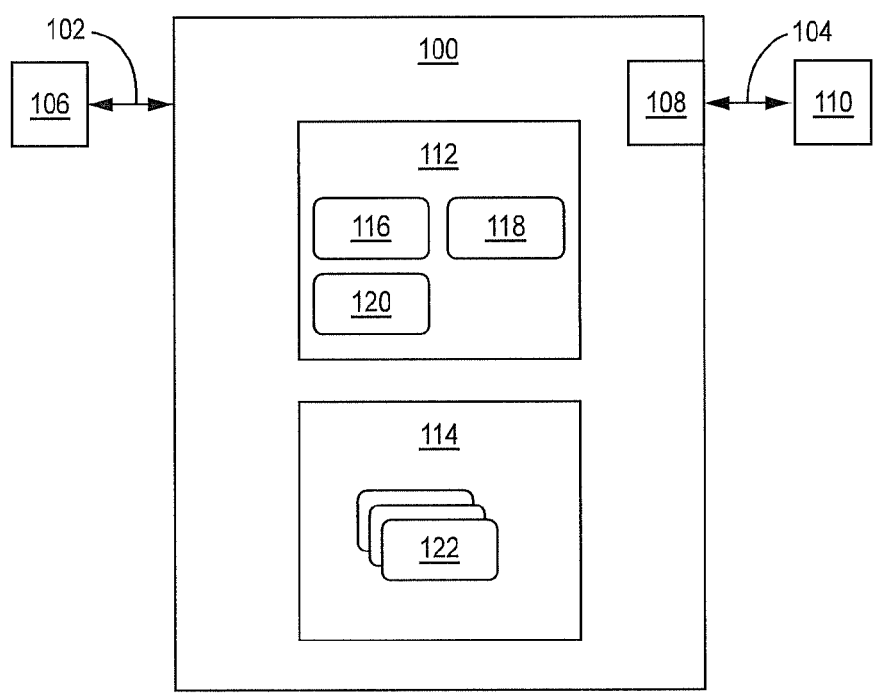
FIG. 3 is an illustration of an example of one controller of the aerosol-generating system.

FIG. 3 shows controller 100 with operative coupling 102 to biosensor 106 and operative coupling 104 to other device 110 using communication interface 108. Controller 100 may be contained in an aerosol-generating device or a charging unit. Other device 110 may be aerosol-generating device 27 (FIGS. 1A-B), charging unit 52 (FIGS. 2A-B), or an external Internet-enabled device separate from the aerosol-generating system. Controller 100 includes processor 112 and memory 114. Processor 112 receives biological characteristic 116 and determines health data 118 based on biological characteristic 116. In some embodiments, biosensor 106 provides health data 118, which is determined by processor 112 when received. Processor 112 determines aerosol delivery profile 120 based on health data 118 and optionally other input received using communication interface 108 or by a user interface (not shown). Memory 114 stores pre-programmed aerosol delivery profiles 122. Aerosol delivery profile 120 may be selected by processor 112 from pre-programmed aerosol delivery profiles 122.

Figure 4:
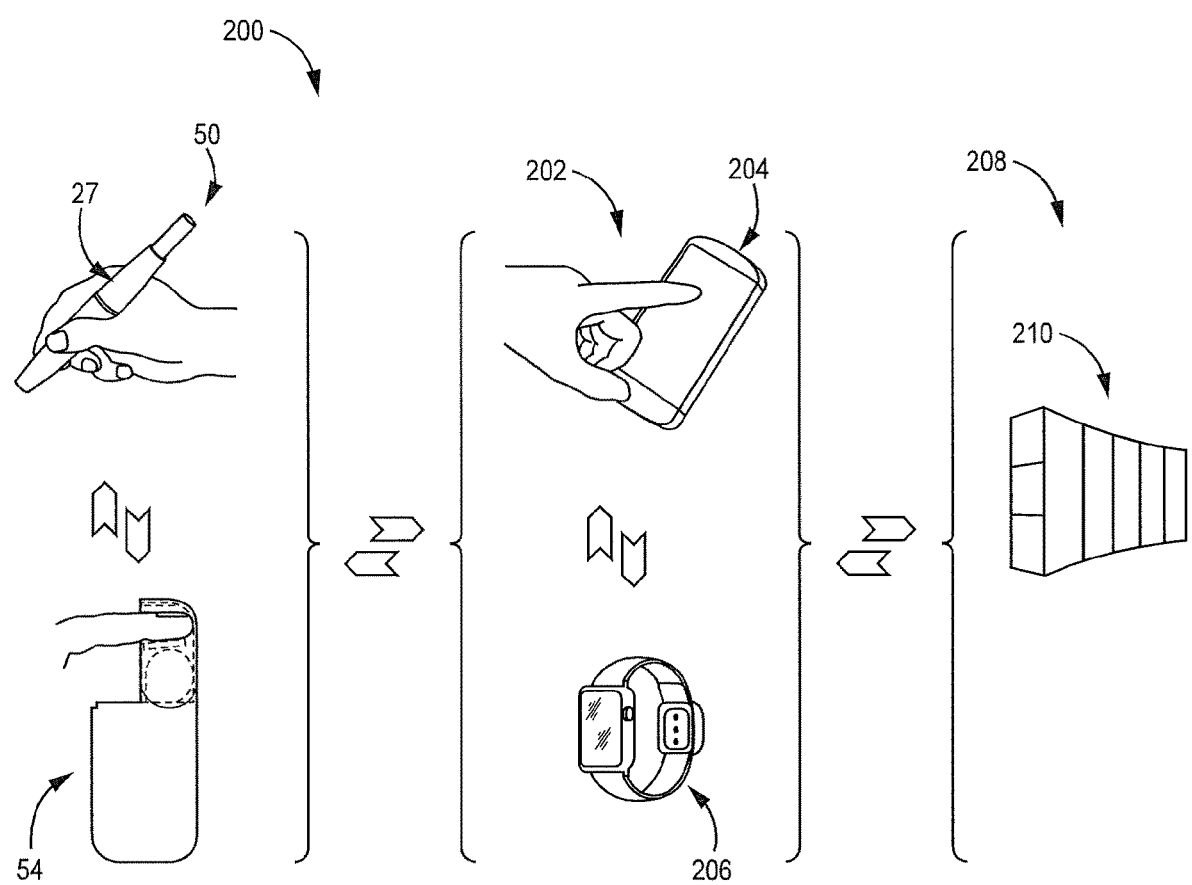
FIG. 4 is an illustration of an example of health data communications using the aerosol-generating system.

FIG. 4 shows a scheme 200 for communicating health data generated and provided by aerosol-generating system 50. Aerosol-generating system 50 includes aerosol-generating device 27 and charging unit 52. Aerosol-generating device 27, charging unit 52, or both aerosol-generating device 27 and charging unit 52 include a biosensor configured to provide health data about the user. One or both of aerosol-generating device 27 and charging unit 52 include a communication interface to at least one Internet-enabled device 202, such as smartphone 204 or wearable 206. In one example, smartphone 204 is Internet-enabled and wearable 206 is operatively coupled to smartphone 204. Health data may be communicated to Internet-enabled device 202 from, or to, aerosol-generating system 50. Internet-enabled device 202 need not be actively connected to the Internet in order to communicate with aerosol-generating system 50. Preferably, at least one Internet-enabled device 202 is operatively couplable over the Internet to remote system 208. Remote system 208 includes remote server 210. Health data may be communicated to remote system 208 for storage, processing, or later access.

The specific embodiments described above are intended to illustrate the invention. However, other embodiments may be made without departing from the scope of the invention as defined in the claims, and it is to be understood that the specific embodiments described above are not intended to be limiting.

As used herein, the singular forms "a," "an," and "the" encompass embodiments having plural referents, unless the content clearly dictates otherwise.

As used herein, "or" is generally employed in its sense including "and/or" unless the content clearly dictates otherwise. The term "and/or" means one or all the listed elements or a combination of any two or more of the listed elements.

As used herein, "have," "having," "include," "including," "comprise," "comprising" or the like are used in their open-ended sense, and generally mean "including, but not limited to". It will be understood that "consisting essentially of," "consisting of," and the like are subsumed in "comprising," and the like.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful and is not intended to exclude other embodiments from the scope of the disclosure, including the claims.

The invention claimed is:

1. An aerosol-generating system comprising:
a housing configured to be held by a user;
an aerosolizer coupled to the housing and configured to produce aerosol from an aerosol-forming substrate comprising nicotine;
a charging unit operatively couplable to the housing;
a biosensor integrated into the charging unit and configured to detect at least one biological characteristic of the user; and
a controller configured to:
activate the aerosolizer; and
provide health data based on the at least one biological characteristic detected by the biosensor.

2. The system of claim 1, wherein the biosensor is accessible by the user when using the aerosolizer.

3. The system of claim 1, wherein the at least one biological characteristic comprises at least one of a blood pressure, a heart rate, an oxygen saturation, a carbon monoxide saturation, and a movement indicator.

4. The system of claim 1, wherein the controller comprises a memory configured to store the health data.

5. The system of claim 1, further comprising a display operatively couplable to the controller configured to display graphics based on the health data.

6. The system of claim 5, wherein the controller comprises a communication interface configured to operatively communicate the health data to at least one of the charging unit of the aerosol-generating system and a separate user interface.

7. The system of claim 1, wherein the controller comprises a communication interface configured to operatively communicate the health data to at least one of the charging unit of the aerosol-generating system and a separate user interface.

8. The system of claim 7, wherein the communication interface is configured to communicate health data to an Internet-enabled device.

9. The system of claim 1, wherein the biosensor comprises at least one of a contact blood pressure sensor, a photoplethysmography electronic, an oximeter electronic set, a non-invasive laser sensor, a bio-impedance monitor, and a motion detector.

10. The system of claim 9, wherein the photoplethysmography electronic set is positioned on the charging unit.

11. The system of claim 10, wherein the oximeter electronic set is positioned on the charging unit.

12. The system of claim 11, wherein the oximeter electronic set is contained in a reclosable housing of the charging unit.

13. The system of claim 12, wherein the oximeter electronic set defines a recess in the reclosable housing configured to receive a finger of the user to detect the at least one biological characteristic of the user.

14. The system of claim 1, wherein the controller is configured to modify an aerosol delivery profile based on the health data.

15. The system of claim 14, wherein to modify the aerosol delivery profile comprises the controller using one of a plurality of pre-programmed aerosol delivery profiles stored on the controller.

16. The system of claim 14, further comprising a display operatively couplable to the controller configured to display graphics based on the health data.

17. The system of claim 14, wherein the controller is configured to automatically modify the aerosol delivery profile based on the health data.

18. The system of claim 17, further comprising a display operatively couplable to the controller configured to display graphics based on the health data.

19. The system of claim 17, wherein to modify the aerosol delivery profile comprises the controller using one of a plurality of pre-programmed aerosol delivery profiles stored on the controller.

20. The system of claim 19, further comprising a display operatively couplable to the controller configured to display graphics based on the health data.

* * * * *